(12) United States Patent
Mitani

(10) Patent No.: US 8,802,708 B2
(45) Date of Patent: Aug. 12, 2014

(54) AGRICULTURAL OR HORTICULTURAL BACTERICIDE COMPOSITION AND METHOD OF CONTROLLING PLANT DISEASE

(75) Inventor: Shigeru Mitani, Shiga (JP)

(73) Assignee: Ishihara Sangyo Kaisha, Ltd, Osaka (JP)

( * ) Notice: Subject to any disclaimer, the term of this patent is extended or adjusted under 35 U.S.C. 154(b) by 1172 days.

(21) Appl. No.: 11/665,736

(22) PCT Filed: Oct. 21, 2005

(86) PCT No.: PCT/JP2005/019414
§ 371 (c)(1),
(2), (4) Date: May 15, 2007

(87) PCT Pub. No.: WO2006/043670
PCT Pub. Date: Apr. 27, 2006

(65) Prior Publication Data
US 2009/0124679 A1    May 14, 2009

(30) Foreign Application Priority Data
Oct. 22, 2004 (JP) ................................. 2004-307849

(51) Int. Cl.
*A01N 43/64* (2006.01)
*A01N 59/26* (2006.01)

(52) U.S. Cl.
USPC ......................................... 514/384; 424/405

(58) Field of Classification Search
CPC ..... A01N 43/653; A01N 37/20; A01N 37/34; A01N 37/38; A01N 43/40; A01N 43/50; A01N 47/12; A01N 59/20; A01N 59/26
See application file for complete search history.

(56) References Cited

U.S. PATENT DOCUMENTS

2002/0160054 A1* 10/2002 Lifshitz .......................... 424/604

FOREIGN PATENT DOCUMENTS

| EP | 1031571 A1 | 8/2000 |
|---|---|---|
| EP | 2 255 628 A2 | 12/2010 |
| JP | 2001-192381 A | 7/2001 |
| JP | 2005-272310 A | 10/2005 |
| WO | 98/44801 A1 | 10/1998 |
| WO | 98/53691 A1 | 12/1998 |
| WO | WO 99/21851 A1 | 5/1999 |
| WO | 99/29175 A1 | 6/1999 |
| WO | 02/069713 A1 | 9/2002 |
| WO | 03/039257 A1 | 5/2003 |
| WO | WO 03-053145 A1 | 7/2003 |
| WO | WO 2005/104847 A1 | 11/2005 |

OTHER PUBLICATIONS

English translation of WO 03/053145 to Suzuki et al.*
European Patent Office, Office Action issued Jul. 1, 2011 in counterpart European application No. 05 805 113.7.
Liu et al. CN 1385070 English abstract.
Liu et al. CN 1314083 English abstract.
D. G. Ouimette et al."Comparative Antifungal Activity of Four Phosphonate Compounds Against Isolates of Nine Phytophthora Species" vol. 79, No. 7,1989, pp. 761-767 XP 002 56 1044.
M. E. Fenn et al.: "Quantification of phosphonate and ethyl phosphonate in tobacco and tomato tissues and significance for the mode of action of two phosphonate fungicides" vol. 79, No. 1, 1989, pp. 76-82.
Fenn et al. Phytopathology, 1989l, 79(1), 76-82, abstract only.
Extended European Search Report issued in application No. 09006898.2—1219 dated Jan. 13, 2010.

* cited by examiner

*Primary Examiner* — Kortney L Klinkel
(74) *Attorney, Agent, or Firm* — Sughrue Mion, PLLC

(57) ABSTRACT

The present invention provides a fungicide composition having stable and high harmful bio-organism control effect on crop plants infected with plant diseases due to plant diseases. Specifically, the present invention provides a fungicide composition for agricultural or horticultural use, which comprises: (a) an indole compound represented by formula (I):

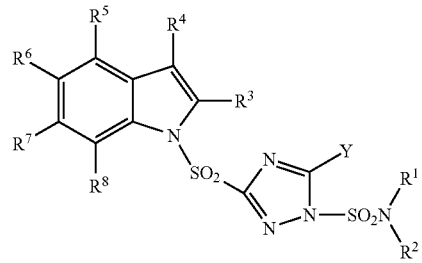

wherein $R^1$ and $R^2$ each independently represents $C_{1-4}$ alkyl, etc.; Y represents H, halogen, etc.; $R^3$ and $R^4$ each independently represents a hydrogen atom, alkyl, etc.; $R^5$, $R^6$, $R^7$ and $R^8$ each independently represents a hydrogen atom, alkyl, etc., and (b) at least other fungicide selected from the group consisting of Dimethomorph, Chlorothalonil, a copper compound, Iprovalicarb, Zoxamide, phosphorous acid or a salt thereof, Fluazinam, Cyazofamid, Flumorph, Benthiavalicarb-isopropyl, Ethaboxam, Methalaxyl-M and Benalaxyl-M.

6 Claims, No Drawings

AGRICULTURAL OR HORTICULTURAL BACTERICIDE COMPOSITION AND METHOD OF CONTROLLING PLANT DISEASE

TECHNICAL FIELD

The present invention relates to a fungicide composition for agricultural or horticultural use in which a plant disease controlling effect, particularly an effect to prevent and/or treat plant disease, has been remarkably improved, and a method for controlling plant disease using the composition.

BACKGROUND ART

Patent Document 1 describes that specific indole compounds are useful as a fungicide for agricultural or horticultural use, and there is a description therein stating that their combined application or concomitant use with other fungicides, insecticides and the like can be carried out, if necessary. Also, Patent Document 2 describes a fungicide composition which comprises one of the above-described indole compounds, 1-(N,N-dimethylsulfamoyl)-3-(3-bromo-6-fluoro-2-methylindol-1-yl)sulfonyl-1,2,4-triazole and Folpet, Cymoxanil, Fosetyl or Mancozeb as active ingredients. In addition, Patent Document 3 describes a production process of 1-(N,N-dimethylsulfamoyl)-3-(3-bromo-6-fluoro-2-methylindol-1-yl)sulfonyl-1,2,4-triazole. On the other hand, Patent Document 4 describes a plant disease controlling composition which comprises (a) at least one auxiliary substance selected from the group consisting of surfactants, animal and plant oils, mineral oils, water-soluble polymers, resins and waxes and (b) 1-(N,N-dimethylsulfamoyl)-3-(3-bromo-6-fluoro-2-methylindol-1-yl)sulfonyl-1,2,4-triazole.

Patent Document 1: International Publication Pamphlet WO 99/21851
Patent Document 2: International Publication Pamphlet WO 03/53145
Patent Document 3: International Publication Pamphlet WO 03/82860
Patent Document 4: JP-A-2005-8566

DISCLOSURE OF THE INVENTION

Problems to be Solved by the Invention

In some cases, the indole compound represented by formula (I) which is described later does not exert sufficient effect on a certain plant disease regarding its plant disease controlling effect, shows a weak treating effect or has a relatively short residual effectiveness, so that it sometimes shows only a practically insufficient controlling effect for plant disease in a certain case of its application.

Means for Solving the Problems

As a result of studies carried out with the aim of solving the above-described problems, the present inventors have obtained information that further superior plant disease controlling effect can be obtained when an indole compound represented by formula (I) which is described later is used by mixing it with a specific fungicide, which cannot be expected in comparison with a case in which each compound is used alone, thus accomplishing the present invention.

That is, the present invention relates to a fungicide composition for agricultural or horticultural use, which comprises:

as an active ingredient (a), at least one indole compound represented by formula (I):

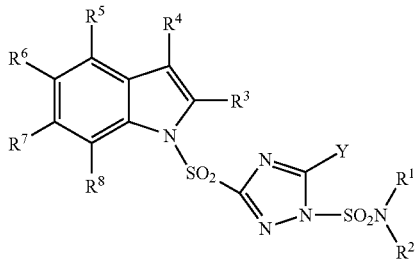

wherein $R^1$ and $R^2$ each independently represents $C_{1-4}$ alkyl, or $C_{4-6}$ alkylene or $C_{4-6}$ alkyleneoxy which is formed by $R^1$ and $R^2$ in combination;

Y represents a hydrogen atom, halogen, cyano, nitro, $C_{1-4}$ alkylsulfonyl, $C_{1-4}$ alkyl, $C_{1-4}$ alkoxy, $C_{1-4}$ alkylthio, $C_{1-4}$ haloalkyl, $C_{1-4}$ haloalkoxy or $C_{1-4}$ haloalkylthio;

$R^3$ and $R^4$ each independently represents a hydrogen atom, $C_4$ alkyl, $C_{3-6}$ cycloalkyl, $C_{2-4}$ alkenyl, $C_{2-4}$ alkynyl, $C_{1-4}$ alkoxy, $C_{1-4}$ alkylthio, halogen, $C_{1-4}$ haloalkyl, nitro, cyano, formyl or ($C_{1-4}$ alkoxy)carbonyl; and $R^5$, $R^6$, $R^7$ and $R^8$ each independently represents a hydrogen atom, $C_{1-4}$ alkyl, $C_{2-4}$ alkenyl, $C_{2-4}$ alkynyl, $C_{1-4}$ alkoxy, $C_{1-4}$ alkylthio, $C_{1-4}$ haloalkyl, $C_{1-4}$ haloalkoxy, $C_{1-4}$ haloalkylthio, $C_{2-4}$ haloalkenyl, $C_{2-4}$ haloalkynyl, ($C_{1-4}$ alkoxy)carbonyl, ($C_{1-4}$ alkyl)carbonyl, ($C_{1-4}$ haloalkyl)carbonyl, ($C_{1-4}$ alkyl)carbonyloxy, $C_{1-4}$ alkylsulfonyl, $C_{1-4}$ haloalkylsulfonyl, $C_{1-4}$ alkylsulfoxy, $C_{1-4}$ alkoxysulfonyl, $C_{1-4}$ alkylsulfonyloxy, cyano, hydroxyl, nitro, formyl or halogen, or $C_{1-3}$ alkylenedioxy or $C_{3-6}$ alkylene which may be substituted with halogen and is formed by two of $R^5$, $R^6$, $R^7$ and $R^8$ in combination, and as an active ingredient (b), at least one selected from the group consisting of Dimethomorph, Chlorothalonil, a copper compound, Iprovalicarb, Zoxamide, phosphorous acid or a salt thereof, Fluazinam, Cyazofamid, Flumorph, Benthiavalicarb-isopropyl, Ethaboxam, Methalaxyl-M and Benalaxyl-M.

In addition, the present invention relates to a method for controlling a plant disease, which comprises applying the above-described fungicide composition for agricultural or horticultural use to a plant.

$C_{1-4}$ alkyl of $R^1$ and $R^2$ in the compound of formula (I) includes, for example, methyl, ethyl, n- or iso-propyl and the like.

$C_{4-6}$ alkylene which is formed by $R^1$ and $R^2$ in combination includes, for example, piperidine and the like including the nitrogen atom to which $R^1$ and $R^2$ are bound.

$C_{4-6}$ alkyleneoxy which is formed by $R^1$ and $R^2$ in combination includes, for example, morpholine and the like, including the nitrogen atom to which $R^1$ and $R^2$ are bound.

Definition of each substituent of Y, $R^3$, $R^4$, $R^5$, $R^6$, $R^7$ and $R^8$ has the following meanings.

$C_{1-4}$ alkyl includes, for example, methyl, ethyl and the like.

$C_{3-6}$ cycloalkyl includes, for example, cyclopropyl, cyclobutyl, cyclopentyl and the like.

$C_{2-4}$ alkenyl includes, for example, allyl, vinyl and the like.

$C_{2-4}$ alkynyl includes, for example, propargyl and the like.

$C_{1-4}$ alkoxy includes, for example, methoxy, ethoxy and the like.

$C_{1-4}$ alkylthio includes, for example, methylthio, ethylthio and the like.

$C_{1-4}$ haloalkoxy includes, for example, trifluoromethoxy and the like.

$C_{1-4}$ haloalkylthio includes, for example, trifluoromethylthio and the like.

$C_{1-4}$ haloalkyl includes, for example, chloromethyl, dichloromethyl, dichlorofluoromethyl, trifluoromethyl and the like.

$C_{2-4}$ haloalkenyl includes, for example, 2-chlorovinyl and the like.

$C_{2-4}$ haloalkynyl includes, for example, iodopropargyl and the like.

($C_{1-4}$ alkoxy)carbonyl includes, for example, methoxycarbonyl and the like.

($C_{1-4}$ alkyl)carbonyl includes, for example, acetyl and the like.

($C_{1-4}$ haloalkyl)carbonyl includes, for example, trifluoroacetyl and the like.

($C_{1-4}$ alkyl)carbonyloxy includes, for example, acetyloxy and the like.

$C_{1-4}$ alkylsulfoxy includes, for example, methylsulfoxy and the like.

$C_{1-4}$ alkylsulfonyl includes, for example, methylsulfonyl, ethylsulfonyl, n-propylsulfonyl, iso-propylsulfonyl, n-butylsulfonyl, sec-butylsulfonyl, iso-butylsulfonyl, tert-butylsulfonyl and the like.

$C_{1-4}$ alkylsulfonyloxy includes, for example, methanesulfonyloxy and the like.

$C_{1-4}$ haloalkylsulfonyl includes, for example, trifluoromethylsulfonyl and the like.

$C_{1-4}$ alkoxysulfonyl includes, for example, methoxysulfonyl and the like.

Halogen includes, fluorine, chlorine, bromine, iodine and the like.

$C_{1-3}$ alkylenedioxy which may be substituted with halogen includes, for example, difluoromethylenedioxy, tetrafluoroethylenedioxy and the like.

Y includes a hydrogen atom, cyano and nitro in addition to those described above.

$R^3$ and $R^4$ include a hydrogen atom, nitro, cyano and formyl in addition to those described above.

$R^5$, $R^6$, $R^7$ and $R^8$ include a hydrogen atom, cyano, hydroxyl, nitro and formyl, in addition to those described above.

The indole compound of formula (I) includes, for example, compounds such as 1-(N,N-dimethylsulfamoyl)-3-(3-bromo-6-fluoro-2-methylindol-1-yl)sulfonyl-1,2,4-triazole (Compound No. 1), 3-(6-fluoro-2-methylindol-1-yl)sulfonyl-1-(N,N-dimethylsulfamoyl)-1,2,4-triazole (Compound No. 2), 3-(2-bromo-3-chloroindol-1-yl)-5-methyl-(N,N-dimethylsulfamoyl)1,2,4-triazole (Compound No. 3), 1-(N, N-dimethylsulfamoyl)-3-(2-methyl-3-chloro-5,6-difluoroindol-1-yl)sulfonyl-1,2,4-triazole (Compound No. 4), and 1-(N,N-dimethylsulfamoyl)-3-(2-methyl-3-chloro-4,6-difluoroindol-1-yl)sulfonyl-1,2,4-triazole (Compound No. 5).

Also, the above-described indole compounds of formula (I) can be produced by the methods described in WO 99/21851, WO 03/82860 and the like.

Dimethomorph, Chlorothalonil, Iprovalicarb, Zoxamide, Fluazinam, Cyazofamid, Flumorph, Benthiavalicarb-isopropyl, Ethaboxam and Metalaxyl-M used in the present invention as the active ingredient (b) are compounds described in *The Pesticide Manual* (13th Edition; BRITISH CROP PROTECTION COUNCIL) pp. 325-326, pp. 169-170, pp. 580-581, pp. 1035-1036, pp. 446-447, pp. 217-218, pp. 462-463, p. 79, p. 374 and pp. 633-635, respectively. Also, Benalaxyl-M (another name Kiralaxyl) is a compound described in *Shibuya Index* (2005) p. 116.

The copper compound used in the present invention as the active ingredient (b) includes, for example, basic copper chloride, cupric hydroxide, basic cupper sulfate, anhydrous copper sulfate and the like. In addition, a mixture of these copper compounds may also be used. The basic copper chloride includes, for example, trade name Doitsu Bordeaux A Dai-ichi Noyaku K. K., Hokko Chemical Industry Co., Ltd.), trade name San Bordeaux (manufactured by Sankei Chemical Co., Ltd.) and trade name Do-jet (Nissan Chemical Industries, Ltd.) can be cited. As the cupric hydroxide, for example, trade name Kocide Bordeaux (manufactured by Griffin), trade name Kocide DF (manufactured by Griffin) and trade name Kocide SD (manufactured by Griffin).

The phosphorous acid or a salt thereof used in the present invention as the active ingredient (b) includes, for example, phosphorous acid, sodium phosphite ($Na_2HPO_3$), potassium phosphite ($K_2HPO_3$), a mixture thereof and the like.

In addition to the active ingredient (a) and active ingredient (b), the fungicide composition for agricultural or horticultural use of the present invention can contain, as an effect reinforcing component (c), at least one selected from the group consisting of a nonionic surfactant, an anionic surfactant, a cationic surfactant, an amphoteric surfactant, animal or plant oil, mineral oil, a water-soluble polymer, a resin and a wax.

The nonionic surfactant used in the present invention as the effect reinforcing component (c) includes, for example, a silicon surfactant; polyoxyethylene fatty acid ester; polyoxyethylene alkyl phenyl ether; a formalin condensate of polyoxyethylene alkyl phenyl ether; polyoxyethylene alkyl ether; a sorbitan higher fatty acid ester surfactant; polyoxyethylene aryl ether; polyoxyethylene (mono-, di- or tri-)phenylphenyl ether; polyoxyethylene (mono-, di- or tri-)benzylphenyl ether; polyoxyproylene (mono-, di- or tri-)benzylphenyl ether; polyoxyethylene (mono-, di- or tri-)styrylphenyl ether; polyoxypropylene (mono-, di- or tri-)styrylphenyl ether; a polymer of polyoxyethylene (mono-, di- or tri-)styrylphenyl ether; a polyoxyethylene polyoxypropylene block polymer; alkyl polyoxyethylene polyoxypropylene block polymer ether; alkyl phenyl polyoxyethylene polyoxypropylene block polymer ether; polyoxyethylene bisphenyl ether; polyoxyethylene resin acid ester; a glycerol fatty acid ester ethylene oxide adduct; a castol oil ethylene oxide adduct, a hardening castol oil ethylene oxide adduct; an alkyl amine ethylene oxide adduct and a fatty acid amide ethylene oxide adduct; polyoxyethylene fatty acid amide; alkyl phenoxy polyethoxy ethanol and polyoxyethylene rosin ester; acetylene surfactants such as acetylene glycol or its ethylene oxide adduct, and acetylene alcohol or its ethylene oxide adduct; and the like.

Specific examples of the above-described silicon surfactant include trade name Makupika (containing 93% polyoxyethylene methyl polysiloxane, manufactured by Ishihara Sangyo Kaisha, Ltd.), trade name DyneAmic (manufactured by STERE CHEMICAL), trade name KINETIC (manufactured by STERE CHEMICAL), SILWET L-77 (manufactured by Witco), trade name SLIPPA (manufactured by INTERAGRO) and the like. Specific examples of the above-described polyoxyethylene fatty acid ester include trade name Pan Guard KS-20 (manufactured by Mitsui Chemicals Crop Life), trade name Spray Sticker (manufactured by NIHON NOYAKU), trade name D-3605 (manufactured by Takemoto Oil and Fat Co., Ltd.), trade name D-230 (manufactured by Takemoto Oil and Fat Co., Ltd.), trade name D-233N (manufactured by Takemoto Oil and Fat Co., Ltd.), trade name Noigen ET-120E (manufactured by Dai-ichi Kogyo Seiyaku Co., Ltd.) and the like.

Specific examples of the above-described sorbitan higher fatty acid ester surfactant include trade name Approach BI (containing 50% polyoxyethylene hexitan fatty acid ester, manufactured by Kao. Corporation), trade name TWEEN 20 (aliphatic acid polyoxyethylene sorbitan ester, manufactured by Wako Pure Chemical Industries) and the like. Specific examples of the other nonionic surfactant include trade name Mix Power (40% polyoxyethylene alkyl phenyl ether and 40% polyoxyethylene alkyl ether, manufactured by Tomono Agrica), trade name Alsoap 30 (containing 30% polyoxyethylene hexitan nonyl phenyl ether, manufactured by Sankei Chemical Co., Ltd. and Takeda Chemical Industries, Ltd.) and the like.

The anionic surfactant used in the present invention as the effect reinforcing component (c) includes, for example, a carboxylic acid surfactant, a sulfuric ester surfactant, a sulfonic acid surfactant, a phosphoric ester surfactant and the like.

The above-described carboxylic acid surfactant includes, for example, polyacrylic acid, polymethacrylic acid, polymaleic acid, a copolymer of maleic acid and olefin (e.g., isobutylene, diisobutylene, etc.), a copolymer of acrylic acid and itaconic acid, a copolymer of methacrylic acid and itaconic acid, a copolymer of maleic acid and styrene, a copolymer of acrylic acid and methacrylic acid, a copolymer of acrylic acid and acrylic acid methyl ester, a copolymer of acrylic acid and vinyl acetate and a copolymer of acrylic acid and maleic acid, and salts of these carboxylic acids and the like.

The above-described sulfuric ester surfactant includes a higher alcohol sulfuric ester salt such as trade name Monogen Y-100 (manufactured by Dai-ichi Kogyo Seiyaku Co., Ltd.); polyoxyethylene alkyl ether sulfuric ester; polyoxyethylene alkyl phenyl ether sulfuric ester; sulfuric ester of a polymer of a polyoxyethylene alkyl phenyl ether; polyoxyethylene benzyl phenyl ether sulfuric ester; polyoxyethylene styryl phenyl ether sulfuric ester; sulfuric esters such as sulfuric ester of a polymer of polyoxyethylene styryl phenyl ether, sulfuric ester of a polyoxyethylene polyoxypropylene block polymer, and sulfated olefin; and salts of these sulfuric esters, and the like.

The above-described sulfonic acid surfactant includes, for example, polyarylalkane sulfonate; dialkyl sulfosuccinate such as Newkalgen EP-70G (manufactured by Takemoto Oil and Fat Co., Ltd.); dialkyl sulfosuccinic acid; alkyl benzene sulfonic acid; α-olefin sulfonic acid; polyoxyethylene alkyl phenyl ether sulfonate; polyoxyethylene alkyl ether sulfosuccinic acid half ester; naphthalene sulfonate, alkyl naphthalene sulfonate, sulfonic acid salts thereof; and the like.

The above-described phosphoric ester surfactant includes, for example, polyoxyethylene alkyl ether phosphoric ester; polyoxyethylene alkyl phenyl ether phosphoric ester; phosphoric ester of a polymer of polyoxyethylene alkyl phenyl ether; polyoxyethylene benzyl phenyl ether phosphoric ester; polyoxyethylene styryl phenyl ether phosphoric ester; phosphoric ester of a polymer of polyoxyethylene styryl phenyl ether and phosphoric ester of a polyoxyethylene polyoxypropylene block polymer; and salts of these phosphoric esters; and the like.

In addition, a mixture of a nonionic surfactant and an anionic surfactant, such as trade name Gramin (containing 15% polyoxypropylene nonyl phenyl ether, 5% polyoxypropylene fatty acid ester and 4% sodium polynaphthylmethanesulfonate, manufactured by Sankyo Agro Co., Ltd.), can also be used in the present invention.

The cationic surfactant used in the present invention as the effect reinforcing component (c) includes, for example, an ethoxylated aliphatic amine surfactant; dialkyl ammonium salt and alkyl ammonium; and the like. Specific examples of the ethoxylated aliphatic amine surfactant include ethoxylated beef tallow amine surfactants such as Frigate, Ethylan TT-15, Genamin T-150, Genamin T-200, Ethomeen T-25, Sorpol 7553, Sorpol 7409 and Newkalgen D-3615T; ethoxylated soybean amine surfactants such as Sorpol 7721 and Newkalgen D-3605; and ethoxylated coconut amine surfactants such as Sorpol 7376, Newkalgen D-3110 and Ethomeen C-12. Also, all of those described above are trade names, and Frigate is manufactured by ISK Biotech; Genamin T-150 and Genamin T-200 are manufactured by Hoechst; Sorpol 7553, Sorpol 7409, Sorpol 7721 and Sorpol 7376 are manufactured by Toho Chemical Industry; and Newkalgen D-3615T, Newkalgen D-3605 and Newkalgen D-3110 are manufactured by Takemoto Oil and Fat Co., Ltd. Also, Ethylan TT-15, Ethomeen T-25 and Ethomeen C-12 are described in *Weed Research*, vol. 20, pp. 139-146, 1980. In addition, Ethylan TT-15 is also described in *Zizaniology*, vol. 2, pp. 183-189, 1990. Specific examples of the dialkyl ammonium salt include trade name Needs (containing 18% dialkyl dimethyl ammonium polynaphthylmethanesulfonate and 44% polyoxyethylene fatty acid ester, manufactured by Kao Corporation) and the like.

The amphoteric surfactant used in the present invention as the effect reinforcing component (c) includes, for example, a betaine surfactant, an amino acid surfactant and the like.

The animal or plant oil used in the present invention as the effect reinforcing component (c) includes, for example, plant oils such as corn oil, soybean oil, linseed oil, sunflower oil, cotton seed oil, rapeseed oil, olive oil, castor oil, palm oil, and avocado oil; animal oils such as beef tallow and whale oil; and the like. These animal and plant oils can be used alone or as a mixture of two or more thereof.

The mineral oil used in the present invention as the effect reinforcing component (c) includes, for example, machine oil, heavy fuel oil, silicon oil, a naphthene solvent, methylnaphthalene, 1-phenyl-1-xylylethane and the like. These mineral oils can be used alone or as a mixture of two or more thereof.

The water-soluble polymer used in, the present invention as the effect reinforcing component (c) is not particularly limited, so long as it is a polymer which is completely dissolved or partially dissolved in water, and examples include natural water-soluble polymers such as starch, dextrin, cellulose, methyl cellulose, ethyl cellulose, carboxymethyl cellulose, hydroxyethyl cellulose, hydroxypropyl cellulose, carboxymethyl starch, pullulan, sodium alginate, ammonium alginate, alginic acid propylene glycol ester, guar gun, locust bean gum, gum arabic, xanthan gum, gelatin, casein, and glue; synthetic water-soluble polymers such as polyvinyl alcohol, polyethylene oxide, polyethylene glycol, ethylene-propylene block polymer, sodium polyacrylate, and polyvinyl pyrrolidone; and the like. These water-soluble polymers can be used alone or as a mixture of two or more thereof. Among the water-soluble polymers, dextrin, carboxymethyl cellulose and polyvinyl pyrrolidone are preferable.

The resin used in the present invention as the effect reinforcing component (c) includes, for example, an acrylic resin, a vinyl acetate resin, a vinyl chloride resin, a urethane resin, a styrene-acryl copolymer resin, a styrene-acrylic acid ester copolymer resin, a vinyl acetate copolymer resin, a vinyl acetate-ethylene copolymer resin, a vinyl acetate-acryl copolymer resin, a vinyl acetate-ethylene-acryl copolymer resin, a vinyl acetate-ethylene-vinyl chloride copolymer resin and the like. These resins can be used alone or as a mixture of two or more thereof. In addition, in the case of their practical use, they are preferably used in the form of emulsion. Among the resins, vinyl acetate resin and urethane resin are preferable.

The wax used in the present invention as the effect reinforcing component (c) includes, for example, paraffin wax, microcrystalline wax, carnauba wax, polyethylene wax, montan wax and the like. These waxes can be used alone or as a mixture of two or more thereof. In addition, in the case of their practical use, they are preferably used in the form of emulsion. Among the waxes, microcrystalline wax, montan wax and polyethylene wax are preferably used.

The fungicide composition for agricultural or horticultural use in the present invention, wherein the above-described active ingredient (a) and active ingredient (b) are used as a mixture, exerts excellent fungicidal activity when applied to cultivating crops which are infected with a harmful disease germ or having a possibility thereof, for example, vegetables such as cucumber, tomato and eggplant; true grass cereals such as rice and wheat; beans; fruit trees such as apple tree, pear tree, grape vine and oranges; potatoes; and the like, and is suitable for controlling diseases such as powdery mildew, downy mildew, anthracnose, gray mold, green mold, scab, alternaria leaf spot, bacterial blight, black spot, melanese, ripe rot, late blight, stephylium leaf spot, blast, sheath blight, damping-off, and sourthen blight. It also exerts excellent effect to control soil disease caused by plant pathogens such as those belonging to the genera *Fusarium, Rhizoctonia, Verticillium* and *Plasmodiophora* excluding Oomycetes, and plant pathogens such as *Pythium* belonging to Oomycetes. The fungicide composition for agricultural or horticultural use in the present invention shows long residual effectiveness and has particularly excellent treating effect, so that disease can be controlled by the treatment after infection. In addition, since it has permeability and translocation property, disease of foliage parts by the soil treatment can also be controlled.

The fungicide composition for agricultural or horticultural use, wherein the above-described active ingredient (a) and effect reinforcing component (c) are used as a mixture, is useful in controlling plant disease, and a part thereof is described in the above-described Patent Document 4. This composition can control, for example, plant pathogens which causes diseases such as rice plant blast, rice plant sheath blight, cucumber anthracnose, cucumber powdery mildew, downy mildew of cucumber, melon, cabbage, Chinese cabbage, onion and grape, late blight of potato, red pepper, green pepper, watermelon, pumpkin, tobacco and tomato, tomato early blight, melanose of citrus fruits, common green mold of citrus fruits, pear scab, apple alternaria leaf spot, various types of gray mold, stem rot, and rust; plant pathogens which cause soil disease such as *Fusarium, Pythium, Rhizoctonia* and *Verticillium*; and the like. More specifically, it can control diseases of potato, red pepper, green pepper, watermelon, pumpkin, tobacco and tomato; diseases caused by Oomycetes, such as downy mildew of cucumber, melon, cabbage, Chinese cabbage, onion and grape, and diseases caused by *Pythium* in rice plant, turf, etc.; and the like. This fungicide composition for agricultural or horticultural use in the present invention shows excellent preventive effect with long residual effectiveness and also has excellent treating effect, so that diseases can be controlled by the treatment after infection.

The fungicide composition for agricultural or horticultural use in the present invention, wherein the above-described active ingredient (a), the above-described active ingredient (b) and the effect reinforcing component (c) are used as a mixture, has both of the characteristics of the fungicide composition for agricultural or horticultural use in the present invention, wherein the above-described active ingredient (a) and the above-described active ingredient (b) are used as a mixture, and the fungicide composition for agricultural or horticultural use in the present invention, wherein the above-described active ingredient (a) and the effect reinforcing component (c) are used as a mixture, so that it can control the plant diseases which can be controlled by both of the compositions.

The two or more of active ingredients (above-described active ingredients (a) and (b) and other agricultural chemicals which are described later) and the effect reinforcing component (c), which constitute the fungicide composition for agricultural or horticultural use in the present invention, can be made into various forms, such as emulsions, dusts, water-dispersible powders, solutions, granules and suspensions, by mixing with various auxiliary agents in the same manner as in the case of the conventional agricultural chemicals preparations. In this case, the above-described active ingredient (a), the above-described active ingredient (b) and the other agricultural chemicals which are described later may be made into a pharmaceutical preparation by mixing together, or may be made into separate pharmaceutical preparations which are mixed thereafter. In carrying out practical use of these preparations, they can be used as such or used by diluting them to a predetermined concentration with a diluent such as water. The auxiliary agents described herein include, for example, a carrier, an emulsifying agent, a suspending agent, a thickener, a stabilizing agent, a dispersing agent, a spreader, a wetting agent, a penetrating agent, an antifreezing agent, an antifoaming agent and the like, which may be optionally added, if necessary. The carrier is classified into a solid carrier and a liquid carrier. The solid carrier includes, for example, animal and plant powders such as starch, sucrose, cellulose powder, cyclodextrin, activated carbon, soybean powder, wheat flour, rice husk powder, wood flour, fish meal and dry milk; mineral powders such as talc, kaolin, bentonite, organic bentonite, calcium carbonate, calcium sulfate, sodium bicarbonate, zeolite, diatomaceous earth, white carbon, clay, alumina, silica, sulfur powder and slaked lime; and the like. The liquid carrier includes, for example, water; plant oils such as soybean oil and cotton seed oil; animal oils such as beef tallow and whale oil; alcohols such as ethyl alcohol and ethylene glycol; ketones such as acetone, methyl ethyl ketone, methyl isobutyl ketone and isophorone; ethers such as dioxane and tetrahydrofuran; aliphatic hydrocarbons such as kerosene, kerosene, lamp oil and liquid paraffin; aromatic hydrocarbons such as toluene, xylene, trimethylbenzene, tetramethylbenzene, cyclohexane and solvent naphtha; halogenated hydrocarbons such as chloroform and chlorobenzene; acid amides such as dimethylformamide; esters such as ethyl acetate ester and fatty acid glycerol ester; nitrites such as acetonitrile; sulfur-containing compounds such as dimethyl sulfoxide; N-methyl-2-pyrrolidone; N,N-dimethylformamide; and the like.

According to the fungicide composition for agricultural or horticultural use in the present invention, the appropriate mixing weight ratio of the active ingredient (a) and the active ingredient (b) is usually from 1:10000 to 10000:1, preferably from 1:1000 to 10000:1, and more preferably from 1:100 to 1000:1.

A method for controlling a harmful bio-organism in which the fungicide composition for agricultural or horticultural use in the present invention is applied to the harmful bio-organism is also included in the present invention. Using the concentration of the active ingredient (a) and the active ingredient (b) of the fungicide composition for agricultural or horticultural use in the present invention cannot be defined, because it varies depending on conditions such as objective crop, using method, form of the preparation, applying amount, applying time, and kind of the pathogenic fungus, but in the case of the foliage treatment, the active ingredient (a) is from 0.01 to 1,000 ppm, and preferably from 0.1 to 500 ppm, as the active ingredient concentration, and the active ingredient (b) is from 0.01 to 10,000 ppm, and preferably from 0.1 to 7,000 ppm.

According to the method of the present invention, other agricultural chemicals such as a fungicide, an insecticide, an acaricide, a nematocide, an antiviral agent, an attractant, a herbicide, a plant growth regulator and the like can be used in combination, and such a case may sometimes show further superior effect. Particularly typical as the other agricultural chemicals are azole compounds such as Triflumizole (common name); quinoxaline compounds such as Chinomethionat (common name); pyridinamine compounds including benzimidazole compounds such as Benomyl (common name); phenylamide compounds such as Metalaxyl (common name) and Oxadixyl (common name); sulfenic acid compounds such as Dichlofluanid (common name); isoxazole compounds such as Hymexazol (common name); dicarboxyimide compounds such as Procymidone (common name); benzanilide compounds such as Flutolanil (common name); benzamide compounds such as (RS)-4-chloro-N-[cyano(ethoxymethyl)]benzamide; β-methoxyacrylic acid compounds such as methyl (E)-2-{2-[6-(2-cyanophenoxy)pyrimidin-4-yloxy]phenyl}-3-methoxyacrylate and methyl (E)-methoxyimino[α-(o-tolyloxy)-O-tolyl]acetate; amino acid amide carbamate compounds, oxazolidinedione compounds such as 3-anilino-5-methyl-5-(4-phenoxyphenyl)-1,3-oxazolidine-2,4-dione; 4-chloro-N-[2-[3-methoxy-4-(propyloxy)phenyl]ethyl]-α-(2-propyloxy)-benzene acetamide; and the like.

According to the fungicide composition for agricultural or horticultural use in the present invention, the appropriate mixing weight ratio of the active ingredient (a) and the active ingredient (b) and the effect reinforcing component (c) is usually from 1:5,000 to 2,000:1, preferably from 0.05:99.95 to 90:10, and more preferably from 0.2:99.8 to 80:20.

The applying concentration and the applying amount of the fungicide composition for agricultural or horticultural use in the present invention cannot be defined generally, because they vary depending on conditions such as objective crop, using method and form of the preparation, but in the case of the foliage treatment, usually, the active ingredient concentration is from 0.1 to 10,000 ppm, and the effect reinforcing component concentration is from 0.01 to 1000 ppm. In the case of the soil treatment, usually, the active ingredient applying amount is from 0.01 to 100 kg/ha, and the effect reinforcing component applying amount is from 0.1 to 10 kg/ha.

Effect of the Invention

According to the present invention, further superior plant disease controlling effect can be obtained when an indole compound represented by formula (I) is used by mixing it with a specific fungicide, which cannot be expected in comparison with a case in which each compound is used alone.

BEST MODE FOR CARRYING OUT THE INVENTION

Next, best mode of the fungicide composition for agricultural or horticultural use in the present invention and that for applying said composition to a plant are described.

As one of the desirable embodiments of the plant disease controlling method of the present invention, a method in which the fungicide composition for agricultural or horticultural use in the present invention is made into a water dispersion and applied to a plant can be exemplified. In this method, the fungicide composition for agricultural or horticultural use is made into a water dispersion and applied to a place where a plant disease is generated or its generation is suspected. As such a place, leaves and stems of a plant for agricultural or horticultural use, soil and the like can be cited, and the effect is particularly notable when the place is leaves and stems of a plant for agricultural or horticultural use. As the water dispersion, those in which the preparations of active ingredients are dispersed in water, and the effect reinforcing component is added thereto; those in which the active ingredients and effect reinforcing component are mixed in advance, and the resulting preparation is dispersed in water; or those in which they are dispersed in water by a method equivalent thereto, are used. At the time of applying a water dispersion, the water dispersion is used by preparing it using 1 liter of water based on from 0.1 to 10,000 mg of the fungicide composition for agricultural or horticultural use. The water dispersion is prepared in such a manner that concentration of the active ingredients becomes from 0.1 to 10,000 ppm. Applying amount of the water dispersion is from 100 to 10,000 liters per 1 ha.

As one of the desirable embodiments of the plant disease controlling method of the present invention, a method in which an aqueous suspension preparation of the fungicide composition for agricultural or horticultural use in the present invention is directly applied to a harmful bio-organism similar to the case of the water dispersion. The aqueous suspension preparation is prepared in such a manner that concentration of the active ingredients becomes from 0.1 to 10,000 ppm. The applying amount of the aqueous suspension preparation is from 100 to 10,000 liters per 1 ha.

Next, some of the desirable embodiments of the fungicide composition for agricultural or horticultural use in the present invention are exemplified, but the present invention is not limited thereto.

(1) A fungicide composition for agricultural or horticultural use in the present invention, wherein the active ingredient (a) is a compound in which, in formula (I), $R^3$ and $R^4$ each independently represents a hydrogen atom, $C_{1-4}$ alkyl, $C_{3-6}$ cycloalkyl, $C_{2-4}$ alkenyl, $C_{2-4}$ alkynyl, $C_{1-4}$ alkoxy, $C_{1-4}$ alkylthio, halogen, $C_{1-4}$ haloalkyl, nitro, cyano, formyl or ($C_{1-4}$ alkoxy)carbonyl; and $R^5$, $R^6$, $R^7$ and $R^8$ each independently represents a hydrogen atom, $C_{1-4}$ alkyl, $C_{2-4}$ alkenyl, $C_{2-4}$ alkynyl, $C_{1-4}$ alkoxy, $C_{1-4}$ alkylthio, $C_{1-4}$ haloalkyl, $C_{1-4}$ haloalkoxy, $C_{1-4}$ haloalkylthio, $C_{2-4}$ haloalkenyl, $C_{2-4}$ haloalkynyl, ($C_{1-4}$ alkoxy)carbonyl, ($C_{1-4}$ alkyl)carbonyl, ($C_{1-4}$ haloalkyl)carbonyl, ($C_{1-4}$ alkyl)carbonyloxy, $C_{1-4}$ alkylsulfonyl, $C_{1-4}$ haloalkylsulfonyl, $C_{1-4}$ alkylsulfoxy, $C_{1-4}$ alkoxysulfonyl, $C_{1-4}$ alkylsulfonyloxy, cyano, hydroxyl, nitro, formyl or halogen.

(2) A fungicide composition for agricultural or horticultural use in the present invention, wherein the active ingredient (a) is at least one compound selected from the group consisting of 1-(N,N-dimethylsulfamoyl)-3-(3-bromo-6-fluoro-2-methylindol-1-yl)sulfonyl-1,2,4-triazole, 3-(6-fluoro-2-methylindol-1-yl)sulfonyl-1-(N,N-dimethylsulfamoyl)-1,2,4-triazole, 3-(2-bromo-3-chloroindol-1-yl)-5-methyl-(N,N-dimethylsulfamoyl)1,2,4-triazole, 1-(N,N-dimethylsulfamoyl)-3-(2-methyl-3-chloro-5,6-difluoroindol-1-yl)sulfonyl-1,2,4-triazole and 1-(N,N-dimethylsulfamoyl)-3-(2-methyl-3-chloro-4,6-didifluoroindol-1-yl)sulfonyl-1,2,4-triazole.

(3) A fungicide composition for agricultural or horticultural use in the present invention, wherein the active ingredient (a) is 1-(N,N-dimethylsulfamoyl)-3-(3-bromo-6-fluoro-2-methylindol-1-yl)sulfonyl-1,2,4-triazole.

(4) A fungicide composition for agricultural or horticultural use in the present invention, which comprises, as an effect reinforcing component (c), at least one selected from the group consisting of a nonionic surfactant, an anionic surfactant, a cationic surfactant, an amphoteric surfactant, an animal or plant oil, a mineral oil, a water-soluble polymer, a resin and a wax, in addition to the active ingredient (a) and active ingredient (b).

(5) The fungicide composition for agricultural or horticultural use described in the above-described (4), wherein the effect reinforcing component (c) is at least one selected from the group consisting of a nonionic surfactant, an anionic surfactant and a cationic surfactant.

(6) The fungicide composition for agricultural or horticultural use described in the above-described (5), wherein the effect reinforcing component (c) is at least one selected from the group consisting of a silicon surfactant, polyoxyethylene fatty acid ester, polyoxyethylene alkyl phenyl ether, polyoxyethylene alkyl ether, a sorbitan higher fatty acid ester surfactant, polyoxyethylene nonyl phenyl ether, polyoxyethylene fatty acid ester, an ethoxylated aliphatic amine surfactant, sodium polynaphthylmethanesulfonate, dialkyl dimethyl ammonium polynaphthylmethanesulfonate and polyoxyethylene fatty acid ester.

(7) The fungicide composition for agricultural or horticultural use described in the above-described (6), wherein the effect reinforcing component (c) is at least one selected from the group consisting of trade name Makupika, trade name Pan Guard, trade name Mix Power, trade name Gramin S, trade name Approach BI, trade name Frigate and trade name Needs.

(8) A fungicide composition for agricultural or horticultural use in the present invention, wherein the mixing weight ratio of the active ingredient (a) and the active ingredient (b) is from 1:10000 to 10000:1.

(9) The fungicide composition for agricultural or horticultural use described in the above-described (4), wherein the mixing weight ratio of the total amount of the active ingredient (a) and the active ingredient (b) with the effect reinforcing component (c) is from 1:5000 to 5000:1.

(10) A method for controlling a plant disease, which comprises applying the fungicide composition for agricultural or horticultural use in the present invention to a plant.

EXAMPLES

Reference Example

Cucumber Downy Mildew Treating Effect Test

Preparation of Water Dispersion:

An effect reinforcing component was dispersed in water to a concentration of from 1,000 times to 10,000 times, and then the above-described Compound No. 1 was added thereto to a concentration of 63 ppm or 16 ppm to thereby prepare a water dispersion. In this case, the spreaders shown in Table 1 and Table 2 were used as the effect reinforcing components. In addition, for the sake of comparison, a predetermined concentration (63 ppm or 16 ppm) of Compound No. 1 liquid containing no effect reinforcing component was prepared in the same manner as the above-described water dispersion.

Organism Test Method and Results:

A cucumber (variety: Sagami Hanjiro) was cultivated in a plastic pot of 7.5 cm in diameter, and when it reached the bifoliate stage, a spore suspension of downy mildew was spray-inoculated thereto. Each of the water dispersions to be tested was sprayed thereto 17 hours thereafter using a spray gun at a ratio of 5 ml per seedling. In addition, the above-described Compound No. 1 liquid was also sprayed in the same manner. After keeping in a constant temperature chamber at 22 to 24° C. for 6 days, area of the lesion on the first leaf was inspected to calculate lesion area ratio (%), with the results shown in Table 1 and Table 2. In addition, each of the theoretical values of the infection ratio calculated based on the Colby's formula was also shown by the parentheses in Table 1 and Table 2. In this connection, results similar to those which are shown in Table 1 and Table 2 are obtained within the same concentration range when a liquid comprising the Compound No. 1 and at least one selected from the group consisting of Dimethomorph, Chlorothalonil, a copper compound, Iprovalicarb, Zoxamide, phosphorous acid or a salt thereof, Fluazinam, Cyazofamid, Flumorph, Benthiavalicarb-isopropyl, Ethaboxam, Methalaxyl-M and Benalaxyl-M was used instead of the Compound No. 1 liquid.

TABLE 1

|  |  | Concentration of Compound No. 1 | | |
| --- | --- | --- | --- | --- |
| Spreader | Dilution ratio | 63 ppm | 16 ppm | 0 ppm |
| Makupika | 3,000 times | 0 (40) | 0 (60) | 100 |
| Pan Guard KS-20 | 1,000 times | 0 (40) | 20 (60) | 100 |
| Mix Power | 3,000 times | 0 (32) | 0 (48) | 80 |
| Gramin S | 10,000 times | 0 (40) | 0 (60) | 100 |
| Gramin S | 1,000 times | 0 (40) | 5 (60) | 100 |
| Approach BI | 1,000 times | 0 (40) | 5 (60) | 100 |
| No mixed use of spreader | | 40 | 60 | 100 |

TABLE 2

|  |  | Concentration of Compound No. 1 | |
| --- | --- | --- | --- |
| Spreader | Dilution ratio | 4 ppm | 0 ppm |
| Frigate | 1,000 times | 0 (30) | 100 |
| Needs | 1,000 times | 4 (30) | 100 |
| No mixed use of spreader | | 30 | 100 |

Test Example 1

Cucumber Downy Mildew Treating Effect Test

A cucumber (variety: Sagami Hanjiro) was cultivated in a plastic pot of 7.5 cm in diameter, and when it reached the bifoliate stage, a spore suspension of downy mildew was spray-inoculated thereto. Each of the liquids to be tested was sprayed thereto 17 hours thereafter using a spray gun at a ratio of 5 ml per seedling. In addition, the above-described Compound No. 1 liquid was also sprayed in the same manner. After keeping in a constant temperature chamber at 22 to 24° C. for 6 days, area of the lesion on the first leaf was inspected to calculate lesion area ratio (%), with the results shown in Table 3 and Table 4. In addition, each of the theoretical values of the infection ratio calculated based on the Colby's formula is also shown by the parentheses in Table 3 and Table 4.

TABLE 3

|  |  | Concentration of Compound No. 1 | | |
| --- | --- | --- | --- | --- |
| Other fungicides | Concentration | 63 ppm | 16 ppm | 0 ppm |
| Potassium phosphite | 250 ppm | 0 (40) | 5 (60) | 100 |
| Ethaboxam | 200 ppm | 0 (12) | 0 (18) | 30 |
| No mixed use of other fungicide | | 40 | 60 | 100 |

TABLE 4

| Other fungicides | Concentration | Concentration of Compound No. 1 | |
|---|---|---|---|
| | | 4 ppm | 0 ppm |
| Dimethomorph | 250 ppm | 0 (30) | 100 |
| Dimethomorph | 350 ppm | 0 (30) | 100 |
| Chlorothalonil | 500 ppm | 8 (30) | 100 |
| Basic copper chloride | 1,000 ppm | 4 (30) | 100 |
| Iprovalicarb | 250 ppm | 0 (30) | 100 |
| Propamocarb | 1,600 ppm | 0 (18) | 60 |
| Zoxamide | 200 ppm | 0 (30) | 100 |
| No mixed use of other fungicide | | 30 | 100 |

Test Example 2

Tomato Late Blight Preventive Effect Test

A tomato (variety: Ponderosa) was cultivated in a plastic pot of 7.5 cm in diameter, and when it reached the tetrafoliate stage, a liquid prepared by adjusting each of the compounds to be tested (Compound No. 1 and other fungicides) to a predetermined concentration was sprayed thereto at a ratio of 10 ml per seedling or sprayed such that applying amount of the liquid became 300 liters per hectare, using a spray gun. A zoosporangium suspension of the late blight fungus was spray-inoculated thereto after 24 hours of the spraying of chemicals. After keeping in a constant temperature chamber at 22 to 24° C. for 3 days, area of the lesion was inspected to calculate lesion area ratio (%). The results are shown in Table 5 to Table 17. In addition, each of the theoretical values of the infection ratio calculated based on the Colby's formula is also shown by the parentheses in Table 5 to Table 17. Also, trade name Doitsu Bordeaux A (Dai-ichi Noyaku K. K. and Hokko Chemical Industry Co., Ltd.) was used as the basic copper chloride, and trade name Kocide Bordeaux (manufactured by Griffin) as the cupric hydroxide, and their concentration was shown as the concentration of copper.

TABLE 5

| Other fungicides | Concentration | Concentration of Compound No. 1 | |
|---|---|---|---|
| | | 1 ppm | 0 ppm |
| Basic copper chloride | 500 ppm | 50 (83) | 100 |
| Basic copper chloride | 1,000 ppm | 75 (83) | 100 |
| Chlorothalonil | 25 ppm | 0 (14) | 17 |
| Chlorothalonil | 13 ppm | 50 (83) | 100 |
| No mixed use of other fungicide | | 83 | 100 |

Sprayed at 10 ml per seedling

TABLE 6

| Benalaxyl-M | Compound No. 1 | | | |
|---|---|---|---|---|
| | 250 g/ha | 100 g/ha | 25 g/ha | 0 g/ha |
| 250 g/ha | 0 (1.96) | 0 (3.91) | 0 (3.91) | 6.25 |
| 100 g/ha | 0 (7.83) | 0 (15.6) | 6.25 (15.6) | 25.0 |
| 25 g/ha | 0 (15.7) | 12.5 (31.3) | 12.5 (31.3) | 50.0 |
| 0 g/ha | 31.3 | 62.5 | 62.5 | 100 |

Sprayed at 300 liters per hectare (250 g/ha corresponds to 833.3 ppm)

Synergistic effect can also be obtained by the same series, Metalaxyl-M, within the same concentration range.

TABLE 7

| Dimethomorph | Compound No. 1 | | | |
|---|---|---|---|---|
| | 250 g/ha | 100 g/ha | 25 g/ha | 0 g/ha |
| 250 g/ha | 0 (19.6) | 12.5 (39.1) | 31.3 (39.1) | 62.5 |
| 100 g/ha | 12.5 (23.6) | 37.5 (46.9) | 31.3 (46.9) | 75.0 |
| 25 g/ha | 18.8 (27.4) | 18.8 (54.7) | 56.3 (54.7) | 87.5 |
| 0 g/ha | 31.3 | 62.5 | 62.5 | 100 |

Sprayed at 300 liters per hectare (250 g/ha corresponds to 833.3 ppm)

TABLE 8

| Flumorph | Compound No. 1 | | | |
|---|---|---|---|---|
| | 250 g/ha | 100 g/ha | 25 g/ha | 0 g/ha |
| 250 g/ha | 0 (3.91) | 0 (7.81) | 0 (7.81) | 12.5 |
| 100 g/ha | 0 (9.80) | 0 (19.6) | 6.25 (19.6) | 31.3 |
| 0 g/ha | 31.3 | 62.5 | 62.5 | 100 |

Sprayed at 300 liters per hectare (250 g/ha corresponds to 833.3 ppm)

TABLE 9

| Fluazinam | Compound No. 1 | | | |
|---|---|---|---|---|
| | 250 g/ha | 100 g/ha | 25 g/ha | 0 g/ha |
| 250 g/ha | 6.25 (11.7) | 6.25 (23.4) | 0 (23.4) | 37.5 |
| 100 g/ha | 6.25 (11.7) | 12.5 (23.4) | 6.25 (23.4) | 37.5 |
| 0 g/ha | 31.3 | 62.5 | 62.5 | 100 |

Sprayed at 300 liters per hectare (250 g/ha corresponds to 833.3 ppm)

TABLE 10

| Chlorothalonil | Compound No. 1 | | |
|---|---|---|---|
| | 100 g/ha | 25 g/ha | 0 g/ha |
| 250 g/ha | 0 (7.83) | 0 (9.38) | 25.0 |
| 100 g/ha | 0 (5.88) | 6.25 (7.05) | 18.8 |
| 0 g/ha | 31.3 | 37.5 | 100 |

Sprayed at 300 liters per hectare (100 g/ha corresponds to 333.3 ppm)

TABLE 11

| Cupric hydroxide | Compound No. 1 | | | |
|---|---|---|---|---|
| | 250 g/ha | 100 g/ha | 25 g/ha | 0 g/ha |
| 2000 g/ha | 0 (11.0) | 12.5 (13.7) | 12.5 (16.4) | 43.8 |
| 800 g/ha | 6.25 (11.0) | 6.25 (13.7) | 25.0 (16.4) | 43.8 |
| 200 g/ha | 6.25 (12.5) | 6.25 (15.7) | 12.5 (18.8) | 50.0 |
| 0 g/ha | 25.0 | 31.3 | 37.5 | 100 |

Sprayed at 300 liters per hectare (2000 g/ha corresponds to 6666.7 ppm)

TABLE 12

| Propamocarb | Compound No. 1 | | | |
|---|---|---|---|---|
| | 250 g/ha | 100 g/ha | 25 g/ha | 0 g/ha |
| 400 g/ha | 12.5 (18.8) | 12.5 (23.5) | 12.5 (38.1) | 75.0 |
| 100 g/ha | 0 (21.9) | 12.5 (27.4) | 18.8 (32.8) | 87.5 |
| 0 g/ha | 25.0 | 31.3 | 37.5 | 100 |

Sprayed at 300 liters per hectare (400 g/ha corresponds to 1333.3 ppm)

TABLE 13

| | Compound No. 1 | | | |
|---|---|---|---|---|
| Iprovalicarb | 250 g/ha | 100 g/ha | 25 g/ha | 0 g/ha |
| 250 g/ha | 0 (1.56) | 0 (1.96) | 0 (2.34) | 6.25 |
| 100 g/ha | 0 (1.56) | 0 (1.96) | 0 (2.34) | 6.25 |
| 25 g/ha | 0 (6.25) | 0 (7.83) | 0 (9.38) | 25.0 |
| 0 g/ha | 25.0 | 31.3 | 37.5 | 100 |

Sprayed at 300 liters per hectare (250 g/ha corresponds to 833.3 ppm)

Synergistic effect can also be obtained by the same series, Benthiavalicarb-isopropyl, within the same concentration range.

TABLE 14

| | Compound No. 1 | | |
|---|---|---|---|
| Ethaboxam | 100 g/ha | 25 g/ha | 0 g/ha |
| 100 g/ha | 0 (1.56) | 0 (2.34) | 6.25 |
| 25 g/ha | 0 (1.56) | 0 (2.34) | 6.25 |
| 0 g/ha | 25.0 | 37.5 | 100 |

Sprayed at 300 liters per hectare (100 g/ha corresponds to 333.3 ppm)

TABLE 15

| | Compound No. 1 | | |
|---|---|---|---|
| Sodium phosphite | 100 g/ha | 25 g/ha | 0 g/ha |
| 1500 g/ha | 0 (12.5) | 6.25 (18.8) | 50.0 |
| 1000 g/ha | 6.25 (18.8) | 25.0 (28.1) | 75.0 |
| 500 g/ha | 12.5 (18.8) | 12.5 (28.1) | 75.0 |
| 0 g/ha | 25.0 | 37.5 | 100 |

Sprayed at 300 liters per hectare (1500 g/ha corresponds to 5000 ppm)

TABLE 16

| | Compound No. 1 | | |
|---|---|---|---|
| Zoxamide | 100 g/ha | 25 g/ha | 0 g/ha |
| 100 g/ha | 6.25 (12.5) | 25.0 (18.8) | 50.0 |
| 25 g/ha | 6.25 (11.0) | 31.3 (16.4) | 43.8 |
| 0 g/ha | 25.0 | 37.5 | 100 |

Sprayed at 300 liters per hectare (100 g/ha corresponds to 333.3 ppm)

TABLE 17

| | Compound No. 1 | | |
|---|---|---|---|
| Cyazofamid | 250 g/ha | 25 g/ha | 0 g/ha |
| 40 g/ha | 6.25 (7.05) | 0 (7.05) | 18.8 |
| 10 g/ha | 0 (9.38) | 12.5 (9.38) | 25.0 |
| 0 g/ha | 37.5 | 37.5 | 100 |

Sprayed at 300 liters per hectare (40 g/ha corresponds to 133.3 ppm)

While the invention has been described in detail and with reference to specific embodiments thereof, it will be apparent to one skill in the art that various changes and modifications can be made therein without departing from the spirit and scope thereof.

This application is based on Japanese application No. 2004-307849 filed on Oct. 22, 2004, the entire contents of which are incorporated hereinto by reference. All references cited herein are incorporated in their entirety.

INDUSTRIAL APPLICABILITY

The present invention provides a fungicide composition for agricultural or horticultural use in which a plant disease controlling effect, particularly an effect to prevent and/or treat plant disease, has been sharply improved, and a method for controlling plant disease using the composition.

The invention claimed is:

1. A fungicide composition for treating a disease of a cultivated crop, which comprises:
    as an active ingredient (a), 1-(N,N-dimethylsulfamoyl)-3-(3-bromo-6-fluoro-2-methylindol-1-yl)sulfonyl-1,2,4-triazole, and
    as an active ingredient (b), phosphorous acid or a salt thereof,
    wherein the mixing weight ratio of (a):(b) is 1:100 to 1000:1.

2. The fungicide composition according to claim 1, which further comprises, as an effect reinforcing component (c), at least one selected from the group consisting of a nonionic surfactant, an anionic surfactant, a cationic surfactant, an amphoteric surfactant, an animal or plant oil, a mineral oil, a water-soluble polymer, a resin and a wax, in addition to the active ingredient (a) and active ingredient (b).

3. The fungicide composition according to claim 1, wherein the effect reinforcing component (c) is at least one selected from the group consisting of a nonionic surfactant, an anionic surfactant and a cationic surfactant.

4. The fungicide composition according to claim 3, wherein the effect reinforcing component (c) is at least one selected from the group consisting of a silicon surfactant, polyoxyethylene fatty acid ester, polyoxyethylene alkyl phenyl ether, polyoxyethylene alkyl ether, a sorbitan higher fatty acid ester surfactant, polyoxyethylene nonyl phenyl ether, polyoxyethylene fatty acid ester, an ethoxylated aliphatic amine surfactant, sodium polynaphthylmethanesulfonate, dialkyl dimethyl ammonium polynaphthylmethanesulfonate and polyoxyethylene fatty acid ester.

5. The fungicide composition according to claim 2, wherein the mixing weight ratio of the total amount of the active ingredient (a) and the active ingredient (b) with the effect reinforcing component (c) is from 1:5000 to 5000:1.

6. A method for controlling a plant disease, which comprises applying the fungicide composition according to claim 1 to a plant in need thereof.

* * * * *

UNITED STATES PATENT AND TRADEMARK OFFICE
CERTIFICATE OF CORRECTION

PATENT NO. : 8,802,708 B2
APPLICATION NO. : 11/665736
DATED : August 12, 2014
INVENTOR(S) : Shigeru Mitani It is certified that error appears in the above-identified patent and that said Letters Patent is hereby corrected as shown below:

In the Claims

Claim 3, column 16, lines 36-39, should read as follows.

3. The fungicide composition according to claim 2, wherein the effect reinforcing component (c) is at least one selected from the group consisting of a nonionic surfactant, an anionic surfactant and a cationic surfactant.

Signed and Sealed this
Tenth Day of February, 2015

Michelle K. Lee
*Deputy Director of the United States Patent and Trademark Office*